US010525118B2

(12) United States Patent
Grode

(10) Patent No.: US 10,525,118 B2
(45) Date of Patent: Jan. 7, 2020

(54) **RECOMBINANT *MYCOBACTERIUM* AS AN IMMUNOTHERAPEUTIC AGENT FOR THE TREATMENT OF CANCER**

(71) Applicant: VAKZINE PROJEKT MANAGEMENT GMBH, Hannover (DE)

(72) Inventor: Leander Grode, Braunschweig (DE)

(73) Assignee: Vakzine Projekt Management GmbH, Hannover (DE)

( * ) Notice: Subject to any disclaimer, the term of this patent is extended or adjusted under 35 U.S.C. 154(b) by 0 days.

(21) Appl. No.: 15/571,415

(22) PCT Filed: May 3, 2016

(86) PCT No.: PCT/EP2016/059872
§ 371 (c)(1),
(2) Date: Nov. 2, 2017

(87) PCT Pub. No.: WO2016/177717
PCT Pub. Date: Nov. 10, 2016

(65) Prior Publication Data
US 2018/0200357 A1 Jul. 19, 2018

Related U.S. Application Data

(60) Provisional application No. 62/387,407, filed on Dec. 23, 2015.

(30) Foreign Application Priority Data

May 4, 2015 (EP) .................................... 15166206

(51) Int. Cl.
*A61K 39/04* (2006.01)
*A61K 39/00* (2006.01)
*A61P 13/10* (2006.01)
*A61P 35/00* (2006.01)

(52) U.S. Cl.
CPC .......... *A61K 39/04* (2013.01); *A61K 39/0011* (2013.01); *A61P 13/10* (2018.01); *A61P 35/00* (2018.01); *A61K 2039/522* (2013.01); *A61K 2039/523* (2013.01); *A61K 2039/541* (2013.01); *A61K 2039/545* (2013.01); *A61K 2039/585* (2013.01)

(58) Field of Classification Search
None
See application file for complete search history.

(56) References Cited

U.S. PATENT DOCUMENTS 7,988,980 B2 * 8/2011 Grode .................... C07K 14/35
424/248.1

FOREIGN PATENT DOCUMENTS

| AU | 2014210617 A1 | 8/2014 | |
|---|---|---|---|
| EP | 1649869 A1 | 4/2006 | |
| WO | 2004094469 A1 | 11/2004 | |
| WO | 2012085101 A1 | 6/2012 | |
| WO | WO-2012085101 A1 * | 6/2012 | ............. A61K 39/04 |
| WO | WO-2012168421 A1 * | 12/2012 | ....... G01N 33/57407 |
| WO | WO-2013111084 A1 * | 8/2013 | ............. A61K 39/04 |

OTHER PUBLICATIONS

Rentsch C.A. et al: "VPM1002—a recombinant BCG with favourable preclinical toxicity and immunogenicity forpotential improvement of BCG immunotherapy for non-muscle invasive bladder cancer", EUR UROL SUPPL, vol. 13, E521, Apr. 11, 2014 (Apr. 11, 2014),~Apr. 15, 2014 (Apr. 15, 2014), XP002746389.
Anonymous: "VPM1002BC in Recurrent Non-muscle Invasive Bladder Cancer", ClinicalTrials.gov, Feb. 10, 2015 (Feb. 10, 2015), XP002746390, Retrieved from the Internet: URL:https://clinicaltrials.govict2/show/NC 102371447 [retrieved on Oct. 12, 2015].
Grode Leander et al: "Safety and immunogenicity of the recombinant BCG vaccine VPM1002 in a phase 1 open-label randomized clinical trial", Vaccine, vol. 31, No. 9, Jan. 3, 2013 (Jan. 3, 2013), pp. 1340-1348, XP028970807.
Kupferschmidt Kai: "Taking a new shot at a TB vaccine.", Science, vol. 334, No. 6062, Dec. 16, 2011 (Dec. 16, 2011), pp. 1488-1490, XP002746391.
Extended European Search Report dated Nov. 10, 2015, Application No. 15166206.1-1403, 13 pages.
International Search Report dated Jul. 22, 2016, Application No. PCT/EP2016/059872, 4 pages.
ClinicalTrials.gov, NCT02371447: "VPM1002BC in Recurrent Non-muscle Invasive Bladder Cancer", First Posted on Feb. 25, 2015, Last Updated on Nov. 7, 2018, 13 pages.
Stefan Kaufmann et al., "The BCG replacement vaccineVPM1OO2: from drawing board to clinical trial", Expert Rev. Vaccines 2014.
Communication pursuant to Article 94(3) EPC cited in application No. 16 724 315.3 dated Dec. 17, 2018, 8 pages.
Rentsch et al., "Bacillus Calmette-Guérin Strain Differences Have an Impact on Clinical Outcome in Bladder Cancer Immunotherapy", European Urology, 66 (2014) 677-688.
Brosch et al., "Genome plasticity of BCG and impact on vaccine efficacy", PNAS, vol. 104, No. 13, Dec. 14, 2007, 6 pages.

* cited by examiner

*Primary Examiner* — Oluwatosin A Ogunbiyi
(74) *Attorney, Agent, or Firm* — Rothwell, Figg, Ernst & Manbeck, P.C.

(57) ABSTRACT

The invention relates to a recombinant *Mycobacterium* cell for use as an immunotherapeutic agent in the treatment of cancer, particularly in the treatment of solid tumors. More particularly, the invention relates to the immunotherapy of bladder carcinoma.

11 Claims, 2 Drawing Sheets
Specification includes a Sequence Listing.

Figure 1 A/B
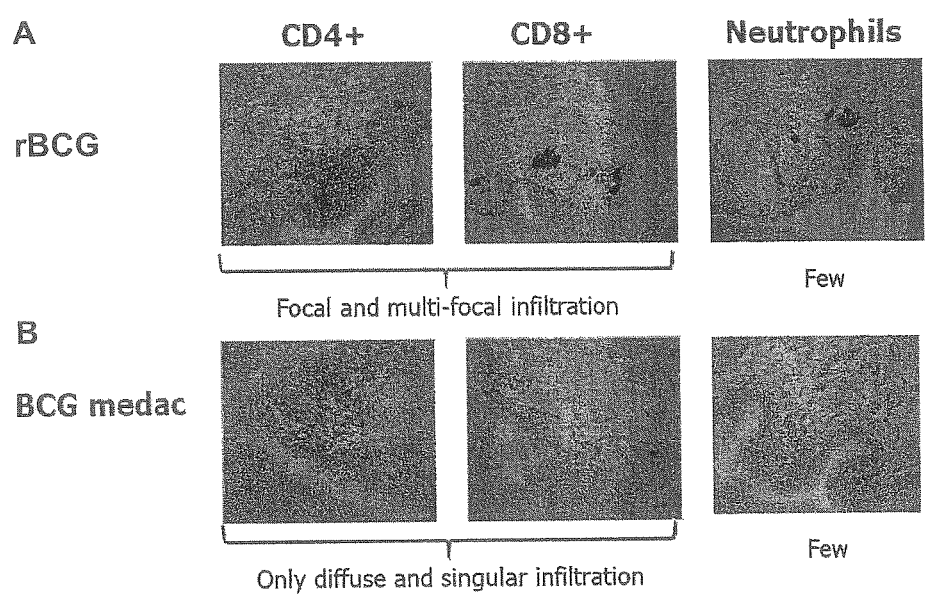

Figure 2 A/B
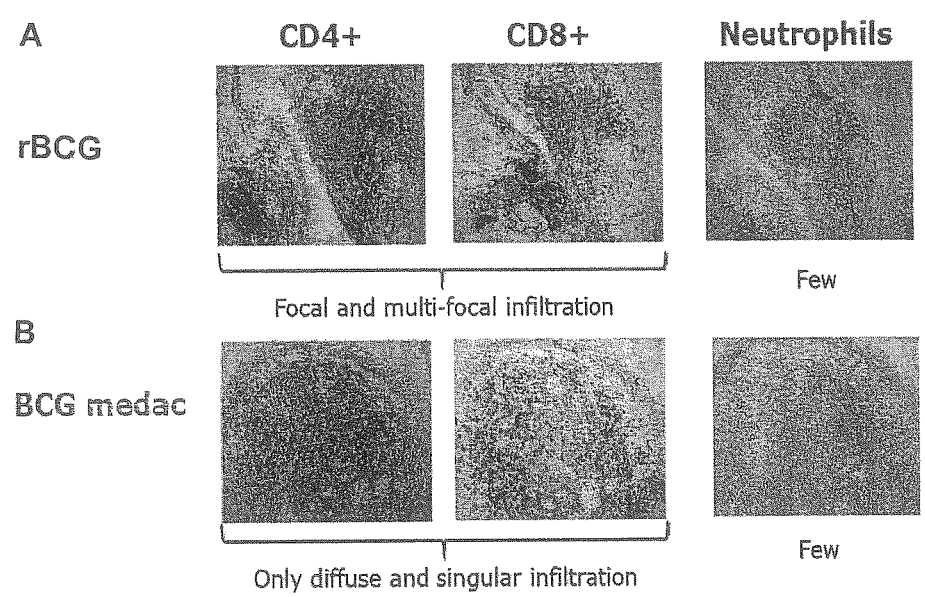

RECOMBINANT *MYCOBACTERIUM* AS AN IMMUNOTHERAPEUTIC AGENT FOR THE TREATMENT OF CANCER

CROSS REFERENCE TO RELATED APPLICATION

This application is a 35 U.S.C. 371 National Phase Entry Application from PCT/EP2016/059872, filed May 3, 2016, which claims the benefit of European Patent Application No. 15166206.1 filed on May 4, 2015 and U.S. Ser. No. 62/387,407, filed Dec. 23, 2015, the disclosures of which are incorporated herein in their entirety by reference.

The invention relates to a recombinant *Mycobacterium* cell for use as an immunotherapeutic agent in the treatment of cancer, particularly in the treatment of solid tumors. More particularly, the invention relates to the immunotherapy of bladder carcinoma.

Urothelial bladder carcinoma is the 5th most common cancer. In the United States, about 75.000 new cases are diagnosed each year 4.5% of all new cancers, and approximately 15.600 deaths are expected. In Germany, about 16.000 new cases are diagnosed each year. Because a recurrence of disease is likely in bladder carcinoma, patients must undergo surveillance for an extended period.

Most bladder carcinomas begin in transitional epithelial cells that make up the inner lining of the bladder. As these tumors grow, they can invade the surrounding connective tissue and muscle. In advanced disease, tumors spread beyond the bladder to nearby lymph nodes or pelvic organs or metastasize to more distant organs such as lung, liver and bone.

The overall 5-year survival rate for bladder carcinoma is 77%, and this rate has not changed significantly over the last 10 years. When considered by stage, the 5-year relative survival rates for patients with tumors restricted to the inner layer of the bladder are 96% and 69%, respectively. The rates drop to 34% for those with disease that has spread locally beyond the bladder and to 6% with distant metastases.

For patients with non-muscle invasive bladder carcinoma, treatment usually involves a surgical removal of the tumor followed by chemotherapy, usually mitomycin C, within the bladder (so-called intravesical chemotherapy). After recovering from surgery, patients with a lower risk of disease progression may undergo surveillance or additional intravesical chemotherapy. Patients with moderate-to-high-grade disease often receive intravesical immunotherapy with an attenuated live bacterium *Bacillus* Calmette Guérin (BCG). BCG was the first FDA-approved immunotherapy and helps reduce the risk of bladder carcinoma recurrence by stimulating an immune response that targets the bacteria as well as any bladder carcinoma cells. In some patients, however, BCG therapy has found to be less effective, particularly after repeated administration.

Standard treatment for patients with muscle-invasive bladder carcinoma includes cisplatin-based chemotherapy followed by surgical removal of the bladder or radiation therapy and concomitant chemotherapy. Recurrent bladder carcinoma may be treated with combination therapy regimens, including gemcitabine plus cisplatin or methotrexate, vinblastine, doxorubicin plus cisplatin.

In the treatment of bladder carcinoma, tumor recurrence is a major concern, even for patients with low-grade disease and requires extensive follow-up. Better treatments, such as novel immunotherapies, might reduce recurrence rates and improve the survival of patients with bladder carcinoma.

A recombinant BCG strain expressing a phagolysosomal escape domain is described in WO 99/10496, the content of which is herein incorporated by reference. The phagolysosomal escape domain enables the strain to escape from the phagosome of infected host cells by perforating the membrane of the phagosome. In order to provide an acidic phagosomal pH for optimal phagolysosomal escape activity, a urease-deficient recombinant strain was developed. This strain is disclosed in WO 2004/094469, the content of which is herein incorporated.

WO 2012/085101, the content of which is herein incorporated, discloses that a recombinant BCG strain expressing membrane-perforating listeriolysin (Hly) of *Listeria monocytogenes* and devoid of urease C induces superior protection against aerogenic challenge with *Mycobacterium tuberculosis* (Mtb) as compared to parental BCG in a preclinical model. Further, it is shown that both the recombinant and the parental strain induce marked Th1 immune responses, whilst only the recombinant BCG strain elicits are profound Th17 response in addition.

In the present study, it was found that a recombinant urease-deficient and listeriolysin-expressing recombinant BCG strain induces a superior immune response compared to the parenteral BCG in an animal model.

A subject-matter of the present invention is a recombinant *Mycobacterium* cell which comprises a recombinant nucleic acid molecule encoding a fusion polypeptide comprising:
(a) a domain capable of eliciting an immune response, and
(b) a phagolysosomal escape domain
for use as an immunotherapeutic agent in the treatment of solid tumors.

A further aspect of the present invention is a method for the immunotherapeutic treatment of solid tumors in a subject in need thereof, comprising administering to said subject a recombinant *Mycobacterium* cell which comprises a recombinant nucleic acid molecule encoding a fusion polypeptide comprising:
(a) a domain capable of eliciting an immune response, and
(b) a phagolysosomal escape domain.

According to the present invention it was found that vesicular instillation of a recombinant BCG cell into the bladder of rats surprisingly results in an increased infiltration of urinary bladder tissue by lymphocytes, particularly CD4- and CD8-positive lymphocytes resulting in a high incidence of focal and/or multifocal lymphocytic infiltration. In contrast thereto, the urinary bladder tissue of animals treated with standard BCG showed CD4- and CD8-positive lymphocytes only as single cell infiltrate levels (diffuse infiltration). Further, administration of a recombinant BCG cell did not raise any safety issues.

Presently, a phase I/II clinical trial assessing safety and efficacy of intravesical instillation of recombinant BCG in human patients with recurrent non-muscle invasive bladder carcinoma after standard BCG therapy is conducted.

Thus, the present invention also relates to a recombinant *Mycobacterium* cell as described above for use as an immunotherapeutic agent in the treatment of solid tumors in order to obtain focal and/or multifocal lymphocytic infiltration, e.g. with CD4 and CD8 T cells at the site of administration. The recombinant *Mycobacterium* cell of the present invention is particularly suitable for use in human medicine.

The immunotherapeutic agent is a live recombinant *Mycobacterium* cell which comprises a recombinant nucleic acid molecule encoding a fusion polypeptide comprising (a) a domain capable of eliciting an immune response and (b) a phagolysosomal escape domain. The domain capable of eliciting an immune response is preferably an immunogenic peptide or polypeptide from a pathogen or an immunogenic fragment thereof.

The *Mycobacterium* cell is preferably an *M. bovis* cell, an *M. tuberculosis* cell, particularly an attenuated *M. tuberculosis* cell or other Mycobacteria, e.g. *M. microti, M. smegmatis, M. canettii, M. marinum* or *M. fortuitum*. More preferably, the cell is an attenuated recombinant *M. bovis* (BCG) cell, particularly an *M. bovis* BCG cell, more particularly a recombinant *M. bovis* BCG cell from strain Danish subtype Prague (Brosch et al., Proc. Natl. Acad. Sci. USA, 104 (2007), 5396-5601). In an especially preferred embodiment, the *Mycobacterium* cell is recombinant urease-deficient. In an especially preferred embodiment the ureC sequence of the *Mycobacterium* cell is inactivated (ΔUrec), e.g. by constructing a suicide vector containing a ureC gene disrupted by a selection marker gene, e.g. the hygromycin gene, transforming the target cell with the vector and screening for selection marker-positive cells having a urease negative phenotype. In an even more preferred embodiment, the selection marker gene, i.e. the hygromycin gene, is subsequently inactivated. In this embodiment, the cell is a selection marker-free recombinant *Mycobacterium* cell. Most preferably, the cell is selection marker-free recombinant BCG strain Danish subtype Prague characterized as recombinant BCG ΔUrec::Hly+.

The domain capable of eliciting an immune response is preferably selected from immunogenic peptides or polypeptides from *M. bovis, M. tuberculosis* or *M. leprae* or from immunogenic fragments thereof having a length of at least 6, preferably at least 8 amino acids, more preferably at least 9 amino acids and e.g. up to 20 amino acids. Specific examples for suitable antigens are Ag85B (p30) from *M. tuberculosis*, Ag85B (α-antigen) from *M. bovis* BCG, Ag85A from *M. tuberculosis* and ESAT-6 from *M. tuberculosis* and fragments thereof. In other embodiments, the domain capable of eliciting an immune response is selected from non-*Mycobacterium* polypeptides.

More preferably, the immunogenic domain is derived from the antigen Ag85B. Most preferably, the immunogenic domain comprises the sequence from aa.41 to aa.51 in SEQ ID No.2.

The recombinant nucleic acid molecule further comprises a phagolysosomal escape domain, i.e. a polypeptide domain which provides for an escape of the fusion polypeptide from the phagolysosome into the cytosol of mammalian cells. Preferably, the phagolysosomal escape domain is a *Listeria* phagolysosomal escape domain, which is described in U.S. Pat. No. 5,733,151, herein incorporated by reference. More preferably, the phagolysosomal escape domain is derived from the listeriolysin gene (Hly) of *L. monocytogenes*. Most preferably, the phagolysosomal domain is encoded by a nucleic acid molecule selected from: (a) a nucleotide sequence comprising nucleotides 211-1722 as shown in SEQ ID No.1, (b) a nucleotide sequence which encodes the same amino acid sequence as the sequence from (a), and (c) a nucleotide sequence hybridizing under stringent conditions with the sequence from (a) or (b).

Apart from the nucleotide sequence depicted in SEQ ID No.1 the present invention also comprises nucleic acid sequences hybridizing therewith. In the present invention the term "hybridization" is used as defined in Sambrook et al. (Molecular Cloning. A laboratory manual, Cold Spring Harbor Laboratory Press (1989), 1.101-1.104). In accordance with the present invention the term "hybridization" is used if a positive hybridization signal can still be observed after washing for one hour with 1×SSC and 0.1% SDS at 55° C., preferably at 62° C. and more preferably at 68° C., particularly for 1 hour in 0.2×SSC and 0.1% SDS at 55° C., preferably at 62° C. and more preferably at 68° C. A sequence hybridizing with a nucleotide sequence as per SEQ ID No.1 under such washing conditions is a phagolysosomal escape domain encoding nucleotide sequence preferred by the subject invention.

A nucleotide sequence encoding a phagolysosomal escape domain as described above may be directly obtained from a *Listeria* organism or from any recombinant source e.g. a recombinant *E. coli* cell containing the corresponding *Listeria* nucleic acid molecule or a variant thereof as described above.

Preferably, the recombinant nucleic acid molecule encoding for a fusion polypeptide contains a signal peptide encoding sequence. More preferably, the signal sequence is a signal sequence active in Mycobacteria, preferably in *M. bovis*, e.g. a native *M. bovis* signal sequence. A preferred example of a suitable signal sequence is the nucleotide sequence coding for the Ag85B signal peptide which is depicted in SEQ ID No.1 from nucleotide 1 to 120.

Further, it is preferred that a peptide linker be provided between the immunogenic domain and the phagolysosomal escape domain. Preferably, said peptide linker has a length of from 5 to 50 amino acids. More preferably, a sequence encoding a linker as shown in SEQ ID No.1 from nucleotide 154 to 210 or a sequence corresponding thereto as regards the degeneration of the genetic code.

The nucleic acid may be located on a recombinant vector. Preferably, the recombinant vector is a prokaryotic vector, i.e. a vector containing elements for replication or/and genomic integration in prokaryotic cells. Preferably, the recombinant vector carries the nucleic acid molecule of the present invention operatively linked with an expression control sequence. The expression control sequence is preferably an expression control sequence active in Mycobacteria, particularly in *M. bovis*. The vector can be an extrachromosomal vector or a vector suitable for integration into the chromosome. Examples of such vectors are known to the man skilled in the art and, for instance, given in Sambrook et al. supra.

The immunotherapeutic agent of the present invention is suitable for the treatment of solid tumors, such as bladder, lung, liver, breast, kidney or prostate tumors. Particularly, the present invention is suitable for the treatment of non-invasive solid tumors. In an especially preferred embodiment, the solid tumor is bladder carcinoma, e.g., non-invasive bladder carcinoma, e.g. non-invasive papillary carcinoma in situ ($T_a$), non-invasive carcinoma in situ ($T_{cis}$), tumor invading subepithelial connective tissue ($T_1$), tumor invading superficial muscle (inner half) ($T_{2a}$), tumor invading deep muscle (outer half) ($T_{2b}$), tumor invading perivesical tissue ($T_3$ including $T_{3a}$ and $T_{3b}$), tumor invading prostate, uterus or vagina ($T_{4a}$), and tumor invading pelvic wall or abdominal wall ($T_{4b}$). Particularly, the tumor is a superficial tumor or carcinoma in situ ($T_{cis}$), non-invasive papillary carcinoma ($T_a$), or a tumor invading subepithelial connective tissue ($T_1$). The immunotherapeutic treatment is suitable for the treatment of primary tumors and/or for the treatment of recurring tumors.

The immunotherapeutic agent is preferably locally administered to the tumor site, i.e., to the site of a primary tumor before surgery or after surgery and optionally after chemotherapy. For the treatment of urothelial bladder carcinoma, the agent is preferably administered by vesicular instillation into the urinary bladder. For other tumors, the administration may involve local injection or, in case of lung tumors, pulmonal administration.

The immunotherapeutic agent of the invention may be administered as a first-line immunotherapy in patients, who have not been treated previously with an anti-tumor-immunotherapeutic agent such as standard BCG, or a follow-up immunotherapy in patients who have been treated previously with anti-tumor-immunotherapeutic agent such as standard BCG. The immunotherapeutic agent may be administered with a newly diagnosed solid tumor, e.g., a bladder carcinoma, or to patients, particularly patients with recurrent solid tumors, e.g., bladder carcinoma.

The immunotherapeutic agent is administered to the subject to be treated in an effective dose. For a human subject, the dose for an administration may be about $10^6$ to $10^{10}$ viable units (CFU), e.g. about $10^7$ to $10^9$ or $10^8$ to $10^9$ viable units. Preferably, the immunotherapeutic agent is administered several times, e.g. at least 3 times or at least 5 times up to 30 times, particularly about 15 times, at predetermined times during the treatment.

The immunotherapeutic agent is usually provided as a pharmaceutical preparation which comprises the recombinant Mycobacterial cell in solid form, e.g., a lyophilized or cryoconserved preparation, which is reconstituted with a suitable liquid carrier before use. Alternatively, the preparation may be provided in liquid form, e.g., as suspension.

In one embodiment, the immunotherapeutic agent of the invention is administered for the treatment of carcinoma in situ. A standard schedule may comprise weekly administration of the agent for at least 4, e.g., 4, 5, 6, 7 or 8 weeks as an induction therapy. The induction therapy should not start until 2-3 weeks after primary tumor surgery. After a treatment-free interval of, e.g., 4 weeks, administration may continue using maintenance therapy for at least 6 months or at least 1 year.

In a further embodiment, the immunotherapeutic agent is administered in an induction therapy in the prophylactic treatment of tumor recurrence. In this embodiment, therapy may start about 2-3 weeks after biopsy of the tumor site and be repeated, e.g., at weekly intervals for at least 4, e.g., 4, 5, 6, 7 or 8 weeks. In intermediate and high-risk tumors this may be followed by maintenance therapy.

Maintenance therapy may comprise long-term therapy, e.g., 6, 9 or 12 months therapy or even longer with treatments at monthly intervals. Alternatively, maintenance therapy may comprise 2, 3 or 4 administrations at weekly intervals, at month 3, 6, 12, 18, 24, 30 and 36.

In still a further embodiment, the immunotherapeutic agent, particularly recombinant BCG ΔUrec::Hly+, is used for the treatment of non-muscle invasive bladder cancer in patients with recurrence after standard BCG therapy. The immunotherapeutic agent is administered into the bladder according to a schedule involving weekly installations during an induction phase with e.g. 6 weekly installations, a first maintenance phase after about 3 months with e.g. 3 weekly installations, a second maintenance phase after about 6 months with e.g. 3 installations and a third maintenance phase after about 12 months with e.g. 3 installations.

The administration as immunotherapeutic agent of the recombinant *Mycobacterium* cell to site of a solid tumor as described above, may be combined with further anti-tumor therapy, e.g., radiation and/or chemotherapy. Further, the immunotherapy as described above, may be combined with a non-tumor site specific administration of the recombinant *Mycobacterium* cell in order to provide a general stimulation of the immune system. This non-site specific administration may be effected as described in WO 2012/085101, e.g.

before surgery of the primary tumor. In this case, the agent is preferably administered to a human subject in a dose of about $1-10 \times 10^5$, preferably about $2-8 \times 10^5$ cells. The agent is preferably administered as a single dose, e.g., by injection. Subcutaneous injection is preferred. Further it is preferred to administer the agent without adjuvant.

Further, the invention is described in more detail by the following Figures and Examples 1-3.

The immunotherapeutic agent "rBCG" used in these examples is recombinant *M. bovis* (BCG) Danish subtype Prague with an inactivated ureC sequence (ΔUrec) and without functional selection marker gene which expresses an Ag85B/Hly fusion protein as shown in SEQ ID No.2 (Hly+).

Example 1

Single Dose Toxicity Study of Recombinant BCG (RBCG) in Rats Following Intravesicular Instillation 1.1 Conduct of Study

| Test item | rBCG lyophilized (rBCG Danish subtype Prague ΔUrec::Hly+ w/o functional selection marker gene) |
|---|---|
| Approximate viable counts | $5.41 \times 10^8$ CFU/vial |
| Reference item | BCG medac |
| Approximate viable counts | $2 \times 10^8$ to $2 \times 10^9$ CFU/vial |
| Test species/Strain/Stock | Rat/CD ®/Crl:CD(SD) |
| Breeder | Charles River Laboratories, Research Models, and Services, Germany GmbH Sandhofer Weg 7 97633 Sulzfeld, Germany |
| Number and sex of animals | 23 female animals; 3 animals for group 1; 5 animals for groups 2 to 5. |
| Dose regime | Group 1: Control (diluent) |
| | Group 2: ~$2 \times 10^6$ CFU rBCG (lyophilized)/animal |
| | Group 3: ~$2 \times 10^8$ CFU rBCG (lyophilized)/animal |
| | Group 4: ~$2 \times 10^6$ CFU rBCG (frozen w/o cryoprotectant)/animal |
| | Group 5: ~$2 \times 10^6$ CFU BCG medac/animal |
| Route of administration | Intravesical instillation in the bladder |
| Frequency of administration | Single dose on test day 1. |
| Administration volume | 500 μL/animal |
| Duration of study | 12 adaptation days 4 in-life test weeks 28 incubation days |

1.2 Results

| Mortality | None of the animals died prematurely. |
|---|---|
| Clinical signs | No changes of behaviour, external appearance or condition of faeces were observed for any animal at any treatment. |
| Body weight | The body weight of all animals of all dose groups was in the normal range throughout the course of the study. |
| Food and drinking water consumption | The food intake of all animals of all dose groups was in the normal range throughout the course of the study. The visual appraisal of the drinking water consumption did not reveal any test or reference item-related influence. |
| IL-2 levels | The IL-2 levels in urine and serum of all animals of all groups were below the lower limit of quantification. |

-continued

| | |
|---|---|
| Macroscopic post mortem findings | No test or reference item-related changes were noted. |
| Organ weights | No test or reference item-related changes were noted. |
| CFU counts | rBCG (groups 2 to 4) vs. control (group 1) No test-item related CFU counts were noted for the examined organs and the blood of the animals treated once with an intravesical instillation of $2 \times 10^6$ or $2 \times 10^8$ CFU rBCG (lyophilized)/animal, or of $2 \times 10^6$ CFU rBCG (frozen)/animal. In particular, no CFU counts at all were noted for the urinary bladder four weeks after instillation of the test item, indicating a rapid clearance of the administered mycobacteria from the site of instillation. No differences were noted between the animals treated with $2 \times 10^6$ or $2 \times 10^8$ CFU rBCG (lyophilized)/animal or with $2 \times 10^6$ CFU rBCG (frozen)/animal and the control animals. BCG medac (group 5) vs. control (group 1) No reference-item related CFU counts were noted for the examined organs and the blood of the animals treated once with an intravesical instillation of $2 \times 10^6$ BCG medac/animal. In particular, no CFU counts at all were noted for the urinary bladder four weeks after instillation of the reference item, indicating a rapid clearance of the administered mycobacteria from the site of instillation. No differences were noted between the animals treated with $2 \times 10^6$ BCG medac/animal and the control animals. rBCG (groups 2 to 4) vs. BCG medac (group 5) No difference in CFU counts was noted for the examined organs and the blood of the animals treated once with an intravesical instillation of $2 \times 10^6$ or $2 \times 10^8$ CFU rBCG (lyophilized)/animal, or of $2 \times 10^6$ CFU rBCG (frozen)/animal compared to the reference group treated in the same way with $2 \times 10^6$ CFU BCG medac/animal. |
| Immunohistochemistry | Immunohistochemistry for lymphocyte subtyping in the urinary bladder tissue revealed the highest incidence of focal and multifocal lymphocytic infiltration with CD4 and CD8 positive cells in groups 2 and 3 treated once with $2 \times 10^6$ or $2 \times 10^8$ CFU rBCG (lyophilized)/animal by intravesical instillation, whereas animals of groups 1 (control), 4 and 5 expressed CD4 and CD8 positive lymphocytes only as single cell infiltrate levels (diffuse infiltration). Nearly all animals (12 of 13) of groups 1 (control), 4 and 5 expressed CD4 and CD8 positive lymphocytes only as single cell infiltrate levels (diffuse infiltration). In contrast nearly all animals (9 of 10) of groups 2 and 3 contained CD4 and CD8 positive lymphocytes in focal or multifocal lymphocyte infiltrates in addition to the diffuse infiltration. Neutrophilic granulocytes could rarely be detected in any slides examined. |

In conclusion, no signs of toxicity were noted for the animals treated with the test item, the reference item or the dilutent. There were no differences in the systemic spread of mycobacteria in blood and organs between rBCG and BCG medac for the treatment by intravesical instillation. No test-item related CFU counts were noted for the examined organs and the blood of the animals treated once with an intravesical instillation of rBCG compared to the control animals. In particular, no CFU counts at all were noted for the urinary bladder 4 weeks after instillation of the test item, indicating a rapid clearance of the administered mycobacteria from the site of instillation.

Immunohistochemistry for lymphocyte sub-typing in the urinary bladder tissue revealed the highest incidence of focal and multifocal lymphocytic infiltration with CD4 and CD8 positive cells in groups 2 and 3 treated once with $2 \times 10^6$ or $2 \times 10^8$ CFU rBCG/animal by intravesical instillation, whereas animals of groups 1 (control), 4 and 5 expressed CD4 and CD8 positive lymphocytes only as single cell infiltrate levels (diffuse infiltration). Nearly all animals (12 of 13) of groups 1 (control), 4 and 5 expressed CD4 and CD8 positive lymphocytes only as single cell infiltrate levels (diffuse infiltration). In contrast, nearly all animals (9 of 10) of groups 2 and 3 contained CD4 and CD8 positive lymphocytes in focal or multifocal lymphocyte infiltrates in addition to the diffuse infiltration. FIG. 1A shows focal and multifocal lymphocytic infiltration after administration of rBCG. FIG. 1B shows only diffuse and singular infiltration after administration of BCG medac (200× magnification).

Example 2

Repeated Dose Toxicity Study of Recombinant BCG (RBCG) in Rats Following Intravesicular Instillation 2.1 Conduct of Study

| | |
|---|---|
| Test item | rBCG lyophilized (rBCG Danish subtype Prague ΔUrec::Hly+ w/o functional selection marker gene) |
| Approximate viable counts | $5.41 \times 10^8$ CFU/vial |
| Reference item | BCG medac |
| Approximate viable counts | $2 \times 10^8$ to $2 \times 10^9$ CFU/vial |
| Test species/Strain/Stock | Rat/CD ®/Crl:CD(SD) |
| Breeder | Charles River Laboratories, Research Models, and Services, Germany GmbH Sandhofer Weg 7 97633 Sulzfeld, Germany |
| Number and sex of animals | 23 female animals; 3 animals for group 1; 5 animals for groups 2 to 5. |
| Dose regime | Group 1: Control (diluent) Group 2: ~$2 \times 10^6$ CFU rBCG (lyophilized)/animal Group 3: ~$2 \times 10^8$ CFU rBCG (lyophilized)/animal Group 4: ~$2 \times 10^6$ CFU rBCG (frozen w/o cryoprotectant)/animal Group 5: ~$2 \times 10^6$ CFU BCG medac/animal |
| Route of administration | Intravesical instillation in the bladder |
| Frequency of administration | Repeated administration; once weekly on test days 1, 8, 15, 22, 29, and 36. |
| Administration volume | 500 μL/animal |
| Duration of study | 21 adaptation days 9 in-life test weeks 28 incubation days |

2.2 Results

| | |
|---|---|
| Mortality | None of the animals died prematurely. |
| Clinical signs | No changes of behaviour, external appearance or condition of faeces were observed for any animal at any treatment. |
| Body weight | The body weight of all animals of all dose groups was in the normal range throughout the course of the study. |

| | -continued |
|---|---|
| Food and drinking water consumption | The food intake of all animals of all dose groups was in the normal range throughout the course of the study. The visual appraisal of the drinking water consumption did not reveal any test or reference item-related influence. |
| IL-2 levels | The IL-2 levels in urine and serum of all animals of all groups were below the lower limit of quantification. |
| Delayed type hypersensitivity (DTH assay) | No delayed type hypersensitivity was noted. |
| Macroscopic post mortem findings | No test or reference item-related changes were noted. |
| Organ weights | No test or reference item-related changes were noted. |
| CFU counts | rBCG (groups 2 to 4) vs. control (group 1) No test-item related CFU counts were noted for the examined organs and the blood of the animals treated six times with an intravesical instillation of $2 \times 10^6$ or $2 \times 10^8$ CFU rBCG (lyophilized)/animal, or of $2 \times 10^6$ CFU rBCG (frozen/w/o cryoprotectant)/animal. In particular, no CFU counts at all were noted for the urinary bladder four weeks after the last instillation of the test item, indicating a rapid clearance of the administered mycobacteria from the site of instillation. No differences were noted between the animals treated with $2 \times 10^6$ or $2 \times 10^8$ CFU rBCG (lyophilized)/animal or with $2 \times 10^6$ CFU rBCG (frozen)/animal and the control animals. BCG medac (group 5) vs. control (group 1) No reference-item related CFU counts were noted for the examined organs and the blood of the animals treated six times with an intravesical instillation of $2 \times 10^6$ BCG medac/animal. In particular, no CFU counts at all were noted for the urinary bladder four weeks after the last instillation of the reference item, indicating a rapid clearance of the administered mycobacteria from the site of instillation. No differences were noted between the animals treated with $2 \times 10^6$ BCG medac/animal and the control animals. rBCG (groups 2 to 4) vs. BCG medac (group 5) No difference in CFU counts was noted for the examined organs and the blood of the animals treated six times with an intravesical instillation of $2 \times 10^6$ or $2 \times 10^8$ CFU rBCG (lyophilized)/animal, or of $2 \times 10^6$ CFU rBCG (frozen)/animal compared to the reference group treated in the same way with $2 \times 10^6$ CFU BCG medac/animal. |
| Immunohistochemistry | Immunohistochemistry for lymphocyte sub-typing in the urinary bladder tissue revealed the highest incidence of multifocal lymphocytic infiltration with CD4 and CD8 positive cells in group 2 treated with $2 \times 10^6$ CFU rBCG/animal by 6 intravesical instillations, followed by group 3 treated with $2 \times 10^8$ CFU rBCG/animal by 6 intravesical instillations, whereas animals of groups 1 (control), 4 and 5 expressed CD4 and CD8 positive lymphocytes only as single cell infiltrate levels (diffuse infiltration). Neutrophilic granulocytes could rarely be detected in any slides examined. |

In conclusion, no signs of toxicity were noted for the animals treated with the test item, the reference item or the diluent. There were no differences in the systemic spread of mycobacteria in blood and organs between rBCG and BCG medac for the treatment by intravesical instillation. No test-item related CFU counts were noted for the examined organs and the blood of the animals treated six times with an intravesical instillation of rBCG compared to the control animals. In particular, no CFU counts at all were noted for the urinary bladder 4 weeks after the last instillation of the test item, indicating a rapid clearance of the administered mycobacteria from the site of instillation.

Immunohistochemistry for lymphocyte sub-typing in the urinary bladder tissue revealed the highest incidence of multifocal lymphocytic infiltration with CD4 and CD8 positive cells in group 2 treated with $2 \times 10^6$ CFU rBCG/animal by 6=intravesical instillations, followed by group 3 treated with $2 \times 10^8$ CFU rBCG/animal by 6 intravesical instillations, whereas animals of groups 1 (control), 4 and 5 expressed CD4 and CD8 positive lymphocytes only as single cell infiltrate levels (diffuse infiltration). FIG. 2A shows focal and multifocal lymphocytic infiltration after administration of rBCG. FIG. 2B shows only diffuse and singular infiltration after administration of BCG medac (200× magnification).

Example 3

Phase I/Ii Open Label Clinical Trial Assessing Safety and Efficacy of Intravesical Instillation of Recombinant BCG (RBCG) in Human Patients with Recurrent Non-Muscle Invasive Bladder Cancer after Standard BCG Therapy 3.1 Clinical Protocol The recombinant BCG (as defined above) is currently applied in clinics as part of a Phase I/II clinical trial by instillation into bladder. The clinical trial phase I/II aims at assessing safety and efficacy of intravesical instillation of rBCG in human patients with recurrent non-muscle invasive bladder cancer after standard BCG therapy. rBCG is administered into bladder in 15 weekly installations (induction phase: instillation 1-6, maintenance 3 months: instillation 7-9, maintenance 6 months: instillation 10-12, maintenance 12 months: instillation 13-15).

The primary endpoint of the phase I is dose limiting toxicity (DLT) of intravesical rBCG installations in patients with recurrence after standard BCG therapy in non-muscle invasive bladder cancer. The DLT period corresponds to 3 installations plus 1 week and covers acute toxicities induced by treatment. Patients are treated in two cohorts of three, following the rules of a 3+3 design (dose de-escalation rules: if patients treated at dose level 1 show signs of DLT, dose of instilled rBCG will be reduced to level −1, which is 10 times lower than level 1).

The dose levels are as follows:
Dose level 1: 1-19.2×10⁸ CFUs of rBCG
Dose level −1: 1-19.2×10⁷ CFUs of rBCG 3.2 Current Status The clinical trial currently is recruiting patients in trial sites in Switzerland (Basel, Geneva, Chur, Bern, Bellinzona, St. Gallen) within the frame of the Phase I.

The DLT period for the first three patients (cohort 1) was completed on 23 Feb. 2016. Safety data, including DLT data, from this cohort has been collected by the sponsor and delivered to the Independent Safety Data Committee (ISDC). Since no DLT has been observed, the next three patients (second cohort) were allowed to be enrolled simultaneously and the recombinant BCG dose was maintained at dose level 1. An approval from the ISDC was received and all parties involved in the trial have been informed about this on 9 Mar. 2016 by the sponsor. In addition, no tumor recurrence has been observed in this cohort of patients at the time of evaluation.

Currently recruitment of the second cohort is ongoing, with the first patient already enrolled in this cohort.

The invention claimed is:

1. A method for the immunotherapy of bladder carcinoma in a human subject in need thereof, comprising administering to said subject a urease C-deficient recombinant *Mycobacterium bovis Bacillus* Calmette-Guerin (BCG) cell from strain Danish subtype Prague as an immunotherapeutic agent, comprising a recombinant nucleic acid molecule encoding a fusion polypeptide comprising:
 (a) a domain capable of eliciting an immune response, and
 (b) a *Listeria* phagolysosomal escape domain listeriolysin (Hly),
 wherein said immunotherapeutic agent is administered by vesicular instillation into said human subject's urinary bladder to produce focal and multifocal lymphocytic infiltration.

2. The method of claim 1, wherein the focal and/or multifocal lymphocytic tissue infiltration is increased compared to administration of native BCG.

3. The method of claim 1, wherein said immunotherapeutic agent is administered to patients with newly diagnosed or recurrent bladder carcinoma who have not been treated previously with standard BCG.

4. The method of claim 1, wherein said immunotherapeutic agent is administered to patients with recurrent bladder carcinoma who have been treated previously with standard BCG.

5. The method of claim 1, wherein the bladder carcinoma is selected from the group consisting of non-invasive bladder carcinoma, non-invasive papillary carcinoma ($T_a$), and a tumor invading subepithelial connective tissue ($T_1$).

6. The method of claim 5, wherein said non-invasive bladder carcinoma is carcinoma in situ ($T_{cis}$).

7. The method of claim 1, wherein the immunotherapeutic agent is administered after surgery.

8. The method of claim 1, wherein the immunotherapeutic agent is administered into the human subject's urinary bladder according to a schedule involving weekly instillations during an induction phase, a first maintenance phase after about 3 months, a second maintenance phase after about 6 months and a third maintenance phase after about 12 months.

9. The method of claim 8, wherein the immunotherapeutic agent is administered into the bladder according to a schedule involving weekly instillations during an induction phase with 6 weekly instillations, a first maintenance phase after about 3 months with 3 weekly instillations, a second maintenance phase after about 6 months with 3 instillations and a third maintenance phase after about 12 months with 3 instillations.

10. The method of claim 1, wherein the immunotherapeutic agent is used at a dose of from about $10^6$ to $10^{10}$ CFU per administration.

11. The method of claim 1, wherein the immunotherapy further comprises a non-tumor site specific administration of the urease C-deficient recombinant *Mycobacterium bovis Bacillus* Calmette-Guerin (BCG) cell from strain Danish subtype Prague.

* * * * *

SEQUENCE LISTING

<160> NUMBER OF SEQ ID NOS: 2

<210> SEQ ID NO 1
<211> LENGTH: 1881
<212> TYPE: DNA
<213> ORGANISM: Artificial Sequence
<220> FEATURE:
<223> OTHER INFORMATION: recombinant nucleic acid molecule
<220> FEATURE:
<221> NAME/KEY: CDS
<222> LOCATION: (1)..(1881)
<223> OTHER INFORMATION: CDS comprising a phagosomal domain (211-1722nt) and a stop codon (1879-1881)

<400> SEQUENCE: 1

```
atg aca gac gtg agc cga aag att cga gct tgg gga cgc cga ttg atg      48
Met Thr Asp Val Ser Arg Lys Ile Arg Ala Trp Gly Arg Arg Leu Met
1               5                   10                  15 atc ggc acg gca gcg gct gta gtc ctt ccg ggc ctg gtg ggg ctt gcc      96
Ile Gly Thr Ala Ala Ala Val Val Leu Pro Gly Leu Val Gly Leu Ala
            20                  25                  30 ggc gga gcg gca acc gcg ggc gcg ttc tcc cgg ccg ggg ctg ccg gtc     144
Gly Gly Ala Ala Thr Ala Gly Ala Phe Ser Arg Pro Gly Leu Pro Val
        35                  40                  45 gag tac ctg cag tct gca aag caa tcc gct gca aat aaa ttg cac tca     192
Glu Tyr Leu Gln Ser Ala Lys Gln Ser Ala Ala Asn Lys Leu His Ser
    50                  55                  60 gca gga caa agc acg aaa gat gca tct gca ttc aat aaa gaa aat tca     240
Ala Gly Gln Ser Thr Lys Asp Ala Ser Ala Phe Asn Lys Glu Asn Ser
65                  70                  75                  80 att tca tcc atg gca cca cca gca tct ccg cct gca agt cct aag acg     288
Ile Ser Ser Met Ala Pro Pro Ala Ser Pro Pro Ala Ser Pro Lys Thr
                85                  90                  95 cca atc gaa aag aaa cac gcg gat gaa atc gat aag tat ata caa gga     336
Pro Ile Glu Lys Lys His Ala Asp Glu Ile Asp Lys Tyr Ile Gln Gly
            100                 105                 110 ttg gat tac aat aaa aac aat gta tta gta tac cac gga gat gca gtg     384
Leu Asp Tyr Asn Lys Asn Asn Val Leu Val Tyr His Gly Asp Ala Val
        115                 120                 125 aca aat gtg ccg cca aga aaa ggt tac aaa gat gga aat gaa tat att     432
Thr Asn Val Pro Pro Arg Lys Gly Tyr Lys Asp Gly Asn Glu Tyr Ile
    130                 135                 140 gtt gtg gag aaa aag aag aaa tcc atc aat caa aat aat gca gac att     480
Val Val Glu Lys Lys Lys Lys Ser Ile Asn Gln Asn Asn Ala Asp Ile
145                 150                 155                 160 caa gtt gtg aat gca att tcg agc cta acc tat cca ggt gct ctc gta     528
Gln Val Val Asn Ala Ile Ser Ser Leu Thr Tyr Pro Gly Ala Leu Val
                165                 170                 175 aaa gcg aat tcg gaa tta gta gaa aat caa cca gat gtt ctc cct gta     576
Lys Ala Asn Ser Glu Leu Val Glu Asn Gln Pro Asp Val Leu Pro Val
            180                 185                 190 aaa cgt gat tca tta aca ctc agc att gat ttg cca ggt atg act aat     624
Lys Arg Asp Ser Leu Thr Leu Ser Ile Asp Leu Pro Gly Met Thr Asn
        195                 200                 205 caa gac aat aaa atc gtt gta aaa aat gcc act aaa tca aac gtt aac     672
Gln Asp Asn Lys Ile Val Val Lys Asn Ala Thr Lys Ser Asn Val Asn
    210                 215                 220 aac gca gta aat aca tta gtg gaa aga tgg aat gaa aaa tat gct caa     720
Asn Ala Val Asn Thr Leu Val Glu Arg Trp Asn Glu Lys Tyr Ala Gln
225                 230                 235                 240
```

-continued

```
gct tat cca aat gta agt gca aaa att gat tat gat gac gaa atg gct      768
Ala Tyr Pro Asn Val Ser Ala Lys Ile Asp Tyr Asp Asp Glu Met Ala
                245                 250                 255 tac agt gaa tca caa tta att gcg aaa ttt ggt aca gca ttt aaa gct      816
Tyr Ser Glu Ser Gln Leu Ile Ala Lys Phe Gly Thr Ala Phe Lys Ala
                260                 265                 270 gta aat aat agc ttg aat gta aac ttc ggc gca atc agt gaa ggg aaa      864
Val Asn Asn Ser Leu Asn Val Asn Phe Gly Ala Ile Ser Glu Gly Lys
        275                 280                 285 atg caa gaa gaa gtc att agt ttt aaa caa att tac tat aac gtg aat      912
Met Gln Glu Glu Val Ile Ser Phe Lys Gln Ile Tyr Tyr Asn Val Asn
    290                 295                 300 gtt aat gaa cct aca aga cct tcc aga ttt ttc ggc aaa gct gtt act      960
Val Asn Glu Pro Thr Arg Pro Ser Arg Phe Phe Gly Lys Ala Val Thr
305                 310                 315                 320 aaa gag cag ttg caa gcg ctt gga gtg aat gca gaa aat cct cct gca     1008
Lys Glu Gln Leu Gln Ala Leu Gly Val Asn Ala Glu Asn Pro Pro Ala
                325                 330                 335 tat atc tca agt gtg gcg tat ggc cgt caa gtt tat ttg aaa tta tca     1056
Tyr Ile Ser Ser Val Ala Tyr Gly Arg Gln Val Tyr Leu Lys Leu Ser
                340                 345                 350 act aat tcc cat agt act aaa gta aaa gct gct ttt gat gct gcc gta     1104
Thr Asn Ser His Ser Thr Lys Val Lys Ala Ala Phe Asp Ala Ala Val
                355                 360                 365 agc gga aaa tct gtc tca ggt gat gta gaa cta aca aat atc atc aaa     1152
Ser Gly Lys Ser Val Ser Gly Asp Val Glu Leu Thr Asn Ile Ile Lys
        370                 375                 380 aat tct tcc ttc aaa gcc gta att tac gga ggt tcc gca aaa gat gaa     1200
Asn Ser Ser Phe Lys Ala Val Ile Tyr Gly Gly Ser Ala Lys Asp Glu
385                 390                 395                 400 gtt caa atc atc gac ggc aac ctc gga gac tta cgc gat att ttg aaa     1248
Val Gln Ile Ile Asp Gly Asn Leu Gly Asp Leu Arg Asp Ile Leu Lys
                405                 410                 415 aaa ggc gct act ttt aat cga gaa aca cca gga gtt ccc att gct tat     1296
Lys Gly Ala Thr Phe Asn Arg Glu Thr Pro Gly Val Pro Ile Ala Tyr
                420                 425                 430 aca aca aac ttc cta aaa gac aat gaa tta gct gtt att aaa aac aac     1344
Thr Thr Asn Phe Leu Lys Asp Asn Glu Leu Ala Val Ile Lys Asn Asn
                435                 440                 445 tca gaa tat att gaa aca act tca aaa gct tat aca gat gga aaa att     1392
Ser Glu Tyr Ile Glu Thr Thr Ser Lys Ala Tyr Thr Asp Gly Lys Ile
450                 455                 460 aac atc gat cac tct gga gga tac gtt gct caa ttc aac att tct tgg     1440
Asn Ile Asp His Ser Gly Gly Tyr Val Ala Gln Phe Asn Ile Ser Trp
465                 470                 475                 480 gat gaa gta aat tat gat cct gaa ggt aac gaa att gtt caa cat aaa     1488
Asp Glu Val Asn Tyr Asp Pro Glu Gly Asn Glu Ile Val Gln His Lys
                485                 490                 495 aac tgg agc gaa aac aat aaa agc aag cta gct cat ttc aca tcg tcc     1536
Asn Trp Ser Glu Asn Asn Lys Ser Lys Leu Ala His Phe Thr Ser Ser
                500                 505                 510 atc tat ttg cca ggt aac gcg aga aat att aat gtt tac gct aaa gaa     1584
Ile Tyr Leu Pro Gly Asn Ala Arg Asn Ile Asn Val Tyr Ala Lys Glu
                515                 520                 525 tgc act ggt tta gct tgg gaa tgg tgg aga acg gta att gat gac cgg     1632
Cys Thr Gly Leu Ala Trp Glu Trp Trp Arg Thr Val Ile Asp Asp Arg
530                 535                 540 aac tta cca ctt gtg aaa aat aga aat atc tcc atc tgg ggc acc acg     1680
Asn Leu Pro Leu Val Lys Asn Arg Asn Ile Ser Ile Trp Gly Thr Thr
```

```
                545                 550                 555                 560
ctt tat ccg aaa tat agt aat aaa gta gat aat cca atc gaa tat gca        1728
Leu Tyr Pro Lys Tyr Ser Asn Lys Val Asp Asn Pro Ile Glu Tyr Ala
                    565                 570                 575 tta gcc tat gga agt cag ggt gat ctt aat cca tta att aat gaa atc        1776
Leu Ala Tyr Gly Ser Gln Gly Asp Leu Asn Pro Leu Ile Asn Glu Ile
            580                 585                 590 agc aaa atc att tca gct gca gtt ctt tcc tct tta aca tcg aag cta        1824
Ser Lys Ile Ile Ser Ala Ala Val Leu Ser Ser Leu Thr Ser Lys Leu
        595                 600                 605 cct gca gag ttc gtt agg cgc gga tcc gga att cga agc tta tcg atg        1872
Pro Ala Glu Phe Val Arg Arg Gly Ser Gly Ile Arg Ser Leu Ser Met
    610                 615                 620 tcg acg tag                                                             1881
Ser Thr
625

<210> SEQ ID NO 2
<211> LENGTH: 626
<212> TYPE: PRT
<213> ORGANISM: Artificial Sequence
<220> FEATURE:
<223> OTHER INFORMATION: Synthetic Construct

<400> SEQUENCE: 2

Met Thr Asp Val Ser Arg Lys Ile Arg Ala Trp Gly Arg Arg Leu Met
1               5                   10                  15

Ile Gly Thr Ala Ala Ala Val Val Leu Pro Gly Leu Val Gly Leu Ala
            20                  25                  30

Gly Gly Ala Ala Thr Ala Gly Ala Phe Ser Arg Pro Gly Leu Pro Val
        35                  40                  45

Glu Tyr Leu Gln Ser Ala Lys Gln Ser Ala Ala Asn Lys Leu His Ser
    50                  55                  60

Ala Gly Gln Ser Thr Lys Asp Ala Ser Ala Phe Asn Lys Glu Asn Ser
65                  70                  75                  80

Ile Ser Ser Met Ala Pro Pro Ala Ser Pro Ala Ser Pro Lys Thr
                85                  90                  95

Pro Ile Glu Lys Lys His Ala Asp Glu Ile Asp Lys Tyr Ile Gln Gly
            100                 105                 110

Leu Asp Tyr Asn Lys Asn Asn Val Leu Val Tyr His Gly Asp Ala Val
        115                 120                 125

Thr Asn Val Pro Pro Arg Lys Gly Tyr Lys Asp Gly Asn Glu Tyr Ile
    130                 135                 140

Val Val Glu Lys Lys Lys Lys Ser Ile Asn Gln Asn Asn Ala Asp Ile
145                 150                 155                 160

Gln Val Val Asn Ala Ile Ser Ser Leu Thr Tyr Pro Gly Ala Leu Val
                165                 170                 175

Lys Ala Asn Ser Glu Leu Val Glu Asn Gln Pro Asp Val Leu Pro Val
            180                 185                 190

Lys Arg Asp Ser Leu Thr Leu Ser Ile Asp Leu Pro Gly Met Thr Asn
        195                 200                 205

Gln Asp Asn Lys Ile Val Val Lys Asn Ala Thr Lys Ser Asn Val Asn
    210                 215                 220

Asn Ala Val Asn Thr Leu Val Glu Arg Trp Asn Glu Lys Tyr Ala Gln
225                 230                 235                 240

Ala Tyr Pro Asn Val Ser Ala Lys Ile Asp Tyr Asp Asp Glu Met Ala
                245                 250                 255
```

-continued

Tyr Ser Glu Ser Gln Leu Ile Ala Lys Phe Gly Thr Ala Phe Lys Ala
          260                 265                 270

Val Asn Asn Ser Leu Asn Val Asn Phe Gly Ala Ile Ser Glu Gly Lys
      275                 280                 285

Met Gln Glu Glu Val Ile Ser Phe Lys Gln Ile Tyr Tyr Asn Val Asn
      290                 295                 300

Val Asn Glu Pro Thr Arg Pro Ser Arg Phe Phe Gly Lys Ala Val Thr
305                 310                 315                 320

Lys Glu Gln Leu Gln Ala Leu Gly Val Asn Ala Glu Asn Pro Pro Ala
              325                 330                 335

Tyr Ile Ser Ser Val Ala Tyr Gly Arg Gln Val Tyr Leu Lys Leu Ser
          340                 345                 350

Thr Asn Ser His Ser Thr Lys Val Lys Ala Ala Phe Asp Ala Ala Val
          355                 360                 365

Ser Gly Lys Ser Val Ser Gly Asp Val Glu Leu Thr Asn Ile Ile Lys
      370                 375                 380

Asn Ser Ser Phe Lys Ala Val Ile Tyr Gly Gly Ser Ala Lys Asp Glu
385                 390                 395                 400

Val Gln Ile Ile Asp Gly Asn Leu Gly Asp Leu Arg Asp Ile Leu Lys
              405                 410                 415

Lys Gly Ala Thr Phe Asn Arg Glu Thr Pro Gly Val Pro Ile Ala Tyr
              420                 425                 430

Thr Thr Asn Phe Leu Lys Asp Asn Glu Leu Ala Val Ile Lys Asn Asn
          435                 440                 445

Ser Glu Tyr Ile Glu Thr Thr Ser Lys Ala Tyr Thr Asp Gly Lys Ile
      450                 455                 460

Asn Ile Asp His Ser Gly Gly Tyr Val Ala Gln Phe Asn Ile Ser Trp
465                 470                 475                 480

Asp Glu Val Asn Tyr Asp Pro Glu Gly Asn Glu Ile Val Gln His Lys
              485                 490                 495

Asn Trp Ser Glu Asn Asn Lys Ser Lys Leu Ala His Phe Thr Ser Ser
          500                 505                 510

Ile Tyr Leu Pro Gly Asn Ala Arg Asn Ile Asn Val Tyr Ala Lys Glu
      515                 520                 525

Cys Thr Gly Leu Ala Trp Glu Trp Trp Arg Thr Val Ile Asp Asp Arg
      530                 535                 540

Asn Leu Pro Leu Val Lys Asn Arg Asn Ile Ser Ile Trp Gly Thr Thr
545                 550                 555                 560

Leu Tyr Pro Lys Tyr Ser Asn Lys Val Asp Asn Pro Ile Glu Tyr Ala
              565                 570                 575

Leu Ala Tyr Gly Ser Gln Gly Asp Leu Asn Pro Leu Ile Asn Glu Ile
          580                 585                 590

Ser Lys Ile Ile Ser Ala Ala Val Leu Ser Ser Leu Thr Ser Lys Leu
      595                 600                 605

Pro Ala Glu Phe Val Arg Arg Gly Ser Gly Ile Arg Ser Leu Ser Met
      610                 615                 620

Ser Thr
625